(12) United States Patent
Chao et al.

(10) Patent No.: US 7,901,695 B2
(45) Date of Patent: Mar. 8, 2011

(54) CONTROLLED RELEASE POLYMERIC GELS

(75) Inventors: Herbert Chao, Paoli, PA (US); Nan Tian, Wilmington, DE (US)

(73) Assignee: Cray Valley USA, LLC, Exton, PA (US)

( * ) Notice: Subject to any disclaimer, the term of this patent is extended or adjusted under 35 U.S.C. 154(b) by 1606 days.

(21) Appl. No.: 10/799,431

(22) Filed: Mar. 12, 2004

(65) Prior Publication Data

US 2004/0180044 A1    Sep. 16, 2004

Related U.S. Application Data

(60) Provisional application No. 60/455,072, filed on Mar. 14, 2003.

(51) Int. Cl.
*A61K 9/00*     (2006.01)
*C08G 18/28*    (2006.01)
*C07C 71/00*    (2006.01)

(52) U.S. Cl. .......... 424/400; 524/195; 525/907; 560/334

(58) Field of Classification Search ............. 424/84, 424/426, 486; 523/102, 122, 179; 524/144; 528/75; 525/66, 123, 127; 604/890.1; 106/15.05, 106/31.25; 560/84, 91
See application file for complete search history.

(56) References Cited

U.S. PATENT DOCUMENTS

| | | | |
|---|---|---|---|
| 3,318,769 A | | 5/1967 | Folckemer |
| 3,639,353 A | * | 2/1972 | Brown ................ 525/329.1 |
| 3,966,837 A | * | 6/1976 | Riew et al. ................ 528/94 |
| 4,189,467 A | | 2/1980 | von Bittera et al. |
| 4,221,572 A | * | 9/1980 | Torimae et al. ............ 51/298 |
| 4,260,718 A | | 4/1981 | Farrissey |
| 4,594,380 A | * | 6/1986 | Chapin et al. ............ 524/144 |
| 6,248,857 B1 | * | 6/2001 | Misumi et al. ............ 528/170 |

FOREIGN PATENT DOCUMENTS

WO    WO 91/19470    12/1991

OTHER PUBLICATIONS

Hawley's Condensed Chemical Dictionary ($13^{th}$ Ed.), p. 215 (1997)—Entry for carboxyl group.*
Hawley's Condensed Chemical Dictionary (13th Ed.), p. 215 (1997)—Entry for carboxyl group.*
MSDS Krasol LBPH 2000.*
Perstorp Product Data Summary.*
Perstorp Polyol 200 TP.*

* cited by examiner

*Primary Examiner* — Robert A Wax
*Assistant Examiner* — Jeffrey T Palenik
(74) *Attorney, Agent, or Firm* — RatnerPrestia

(57) ABSTRACT

A controlled continuous release composition, articles comprising the continuous release composition, methods of using the composition, and methods of preparing the composition are disclosed. The composition comprises an elastomeric matrix which is a reaction product of a carboxyl-terminated polymer with a polycarbodiimide and at least one active agent which is released from the matrix into the environment substantially continuously over an extended period of time.

31 Claims, No Drawings

CONTROLLED RELEASE POLYMERIC GELS

CROSS REFERENCE TO RELATED APPLICATIONS

Benefit of Provisional Application Ser. No. 60/455,072 filed Mar. 14, 2003, is claimed.

BACKGROUND OF THE INVENTION

This invention relates to the field of controlled release of active agents, controlled release compositions, methods, and articles which comprise such compositions. The need for the controlled and sustained release of an active agent into the environment exists in many fields, for instance, in residential and other consumer fields, in agriculture, and in telecommunications.

Matrices that have been used in monolithic controlled release formulations include plasticized polyvinylchloride, rubber (U.S. Pat. No. 3,318,769) and certain polyurethanes (U.S. Pat. Nos. 4,594,380 and 4,189,467). The rubber matrices typically are cured by conventional rubber chemistry, e.g., by sulfur vulcanization or by means of peroxides (U.S. Pat. No. 3,639,583). These curing processes typically comprise a high-temperature step. The high temperature step frequently is a complicating factor when active agents having relatively high vapor pressure, or active agents that are subject to deactivation at the elevated temperature, are to be incorporated into the matrix material. Forming a polyurethane matrix requires polyols to react with isocyanates. Unfortunately, many active ingredients for sustained release contain alcohol functionality which competes with such polyols in the curing reaction. As a result, the polyurethane gel formation is hindered in the presence of alcoholic active ingredients.

Because of the importance of controlled release of active agents, a controlled release system that does not have the shortcomings of prior art systems would be of substantial benefit.

SUMMARY OF THE INVENTION

A first aspect of the present invention is a composition comprising an elastomeric matrix and at least one biologically or non-biologically active agent contained in the matrix which is released from the matrix into the environment substantially continuously over an extended period of time. The matrix can be the reaction product of a hydrophobic or hydrophilic carboxyl-terminated polymer with a polycarbodiimide.

In another aspect, the invention comprises a process comprising reacting hydrophobic or hydrophilic carboxyl-terminated polymer with a polycarbodiimide.

Another aspect of the invention is an article comprised of the matrix composition.

The said hydrophobic carboxyl-terminated polymer comprising a major component selected from the group consisting of carboxyl-terminated polybutadiene, carboxyl-terminated polyisoprene, carboxyl-terminated copolymers of butadiene with acrylonitrile, carboxyl-terminated copolymers of butadiene with styrene, carboxyl-terminated copolymers of isoprene with acrylonitrile, carboxyl-terminated copolymers of isoprene with styrene, and mixtures of the above, the carboxylic acid terminated polymer having an average molecular weight in the range of 1000 to 20000.

The hydrophilic carboxyl-terminated polymer preferably comprises a major component selected from the group consisting of carboxyl-terminated polyethylene oxides, carboxyl-terminated polyether polyols which are copolymers of ethylene oxide and of an alkylene oxide having 3-6 carbons atoms, in an amount of not more than 50 mole percent of said copolymer and having molecular weight from 400 to 20,000.

The polycarbodiimide is preferably selected from the group consisting of the aromatic, cycloaliphatic, aliphatic and heterocyclic carbodiimides, and mixtures of two of more of the above and the said polycarbodiimide having an average functionality higher or equal to 2.

The carbodiimide/carboxylic acid molar ratio, from polycarbodiimide and from carboxyl-terminated polymer, is preferably in the range of 0.7 to 6.0, particularly in the case of a hydrophilic carboxyl-terminated polymer according to b.

More preferably this range is from 0.7 to 1.4, particularly when the said article is not a water-based article, which means when the elastomeric matrix is not based on a hydrophilic carboxyl-terminated polymer, but rather on a hydrophobic one, according to a).

DETAILED DESCRIPTION

Suitable hydrophobic carboxyl-terminated polymers include carboxyl-terminated polybutadienes, carboxyl-terminated polyisoprenes, carboxyl-terminated copolymers of butadiene with acrylonitrile, carboxyl-terminated copolymers of butadiene with styrene, carboxyl-terminated copolymers of isoprene with acrylonitrile, carboxyl-terminated copolymers of isoprene with styrene, and mixtures thereof. The carboxylic acid-terminated polymers preferably have an average molecular weight in the range of 1000 to 20000.

Suitable hydrophilic carboxyl-terminated polymers include, for example, carboxyl-terminated polyethylene oxides, carboxyl-terminated polyether polyols which can be copolymers of ethylene oxide with an alkylene oxide having 3-6 carbon atoms, the alkylene oxide having 3-6 carbon atoms comprising not more than 50 mole percent of said copolymer, wherein the copolymer preferably has a molecular weight from 400 to 20,000.

Suitable polycarbodiimides can be, for example, aromatic, cycloaliphatic, aliphatic, or heterocyclic carbodiimides, and mixtures of two of more thereof. The polycarbodiimides preferably have an average functionality higher or equal to 2.

The carbodiimide/carboxylic acid molar ratio from polycarbodiimide and from carboxyl-terminated polymer is preferably in the range of 0.7 to 6.0. In embodiments wherein the carboxyl-terminated polymer is hydrophobic, this ratio is preferably 0.7 to 1.4.

The article according to the invention comprises an elastomeric matrix and, contained in the matrix material, one or more active agents which are to be released in to the environment substantially continuously over an extended period of time. The elastomer is formed by a process comprising reacting polyacid with carbodiimides. The polyacid or carboxyl-terminated polymer preferably comprises a major component. The major component typically makes up at least 90% by weight of the polyacid and is selected from the group consisting of carboxyl-terminated compounds, such as polybutadiene, polyisoprene, copolymers of butadiene with acrylonitrile, copolymers of butadiene with styrene, copolymers of isoprene with acrylonitrile, copolymers of isoprene with styrene, and mixtures of two or more of the above. The optional minor component is selected from the group consisting of carboxyl-terminated compounds, such as adipic acid, azelaic acid, isophthalic acid and dimer fatty acid. The polyacid preferably has an average molecular weight in the range of 400-20000. The preferred hydrophobic carboxyl-terminated polymer is selected from a carboxyl-terminated polybutadiene having a molecular weight of 1000 to 10000 or a carboxyl-terminated polyisoprene having a molecular weight of 1000 to 10000, and an average carboxylic acid functionality in the range of 1.8 to 8.0.

In addition to the hydrophobic polymers with acid functionality, hydrophilic polymers with carboxylic acid functionality can also be employed and are compatible with water soluble or dispersible ingredients so that the resulting system is more environmentally acceptable. The hydrophilic polyacids consist of carboxyl-terminated polymers such as carboxyl-terminated polyethylene oxides and carboxyl-terminated polyether polyols which are a copolymer of ethylene oxide and an alkylene oxide having 3-6 carbons atoms in an amount of not more than 50 mole percent of $C_3$-$C_6$ alkylene oxide, wherein the polymer has molecular weight 400 to 20000.

The polycarbodiimide is can be aromatic, cycloaliphatic, aliphatic or heterocyclic carbodiimides, or mixtures of two of more thereof. The polycarbodiimides used are preferably produced by subjecting polyfunctional, preferably bifunctional, aliphatic, araliphatic, or, preferably, aromatic isocyanates to carbodiimide formation. Monofunctional or trifunctional and higher functional isocyanates may be used as chain terminators or branching agents for the polycarbodiimides, although they should be employed in quantities of less than about 20% by weight and preferably in quantities of less than about 10% by weight of the total quantity of isocyanate.

Suitable isocyanates include alkyl isocyanates, such as methyl, allyl, butyl, stearyl isocyanate; alkyl diisocyanates such as ethylene diisocyanate, tetramethylene diisocyanate, hexamethylene diisocyanate, isophorone diisocyanate; aromatic monofunctional and bifunctional isocyanates, such as phenyl isocyanate, phenylene diisocyanates, the isomeric toluene diisocyanates, diphenyl methane diisocyanates, dimethyl diphenyl methane diisocyanates, and commercial-grade biphenyl methane diisocyanate mixtures which may optionally contain polynuclear diisocyanates or trifunctional isocyanates as well.

Preferred isocyanates are hexamethylene diisocyanate, isophorone diisocyanate, the toluene diisocyanates and diphenyl methane diisocyanates. The isomers of toluene diisocyanate are preferred.

The matrix optionally may comprise components that do not participate in the crosslinking reaction between polyacid and carbodiimide. Among such "nonreactive" components are comprised: fillers, plasticizers, stabilizers, pigments, and fungicides. Contained in the matrix is the material to be controllably released into the ambient environment, collectively referred to as the active agent.

The active agent can be substantially any biologically or non-biologically active compound that is compatible with the matrix material. Exemplary classes of possible active agent compounds are the aliphatic or aromatic oils, esters, ketones, ethers, halogenated aromatic compounds, alcohols, and organometallics. Fragrances are comprised in these agents. Pheromones may be another class of active agents according to the invention. The active agents according to the present invention are present in an amount of about 10% to 90% by weight based on the total weight of the polymer and the crosslinking agent. In preferred embodiments the active agent is dissolved in the matrix, with the release mechanism comprising diffusion of active agent from the interior of the sample to the release surface. The said agent may also be present dispersed in the said matrix.

The matrix and active agent can be formed into a variety of shapes, combined, if desired, with appropriate containment means, to form an article, preferably in the form of gel, which may be comprised in a related device, providing timed-release biological or non-biological action, e.g., insecticidal, fungicidal, deodorant, molluscidcidal, anti-corrosive, pheromone, antistatic action or antiseptic actions.

Suitable polycarbodiimides have at least 2 carbodiimide groups, preferably at least 3 carbodiimide groups in one molecule. The term "poly" of the "polycarbodiimide" means multiple number of the carbodiimide groups (multifunctional carbodiimide) and does not mean height of molecular weight. The molecular weight of the polycarbodiimide is not limited, but preferably is within the range of 250 to 10,000. All reference to molecular weights herein is to number average molecular weights. The polycarbodiimide is preferably prepared by polycondensation of an organic polyisocyanate in the presence of a carbodiimide promoting agent. The organic polyisocyanate may be, for example, an aromatic polyisocyanate, such as 2,4- or 2,6-toluene diisocyanate, naphthalene 1,5-diisocyanate and diphenylmethane 4,4'-diisocyanate; and an aliphatic or alicyclic polyisocyanate, such as hexamethylene diisocyanate, hydrogenated diphenylmethane 4,4'-diisocyanate, isophorone diisocyanate, and hydrogenated 2,4- or 2,6-toluene diisocyanate.

The carbodiimide promoting agent can be any known to the art, for example as described in Chemical Review, by Andrew Williams, Ibrahim T. Ibrahim, Vo. 81, No. 4, p. 619 (1981). Among them, 1-phenyl-phosphorene-1-oxide, 1-phenyl-3-methyl-phosphorene-1-oxide and 1-ethyl-phosphorene-1-oxide are preferred.

In the preparation of the polycarbodiimide, molecular weight can be controlled by terminating the polycondensation with an organic monoisocyanate, for example as disclosed in J. Appl. Polym. Sci. by L. N. Alberine, Vol 21, p. 1999 (1977). Examples of the organic monoisocyanates are phenyl isocyanate, toluene isocyanate, cyclohexyl isocyanate, butyl isocyanate and the like. A blocking technique in which a terminal isocyanate group is blocked with an active-hydrogen containing compound (a blocking agent) can also control the molecular weight of the polycarbodiimide. The blocking agent is described in detail in for example Progress in Organic Coatings, Vol. 3, p.73 (1975). Typical examples of the blocking agents are alcohols, phenols, lactams, N-hydroxyimide, oximes, imidazoles, triazoles, active methylene compounds (e.g. acetyl acetone and diethyl malonate), aromatic secondary amines, acidic sodium sulfite, and the like.

The preferred carboxyl-terminated polybutadienes are hydrogenated OH-terminated polybutadienes reacted with a stoichiometric amount of 4-methylhexahydrophthalic anhydride (HHMPA).

EXAMPLES

The following examples are presented to illustrate a few of the embodiments of the invention but of course many alternative embodiments can be made according to the invention.

Preparation of Carboxyl-Terminated Polybutadiene

To a 1000-ml resin kettle equipped with an overhead stirrer, heating mantel, inlet and outlet of nitrogen, thermocouple, and condenser is charged the hydroxyl-terminated polybutadiene resin. The resin is heated to 90° C. with stirring under nitrogen and then dried and degassed for 1.5 hrs. at 90° C. in vacuo at <1333 Pa. To the kettle HHMPA is added with stirring at 90° C. The reaction was maintained at 105° C. with stirring under nitrogen for 5 hrs. The viscosity at 30° C. and carboxyl content of four examples of the reaction products are listed in Table 1.

TABLE 1

Viscosity and acid content of carboxyl-terminated polybutadienes

| Identification | Viscosity (cp) at 30° C. | COOH content (meq/g) | wt % |
|---|---|---|---|
| 517-120 (NTX6162) | 90250 | 0.783 | 3.52 |
| 517-121 (NTX6163) | 94000 | 0.583 | 2.62 |
| 517-123 (NTX6162) | 88750 | 0.798 | 3.59 |
| 517-129 (NTX6163) | 88750 | 0.563 | 2.53 |

Specifications of Starting Materials

The equivalent weight, viscosity at 25° C., and Mn of the starting materials used in the following examples are set forth in Table 2.

TABLE 2

Chemicals specifications

| Reactants | Eq. Wt. | Viscosity @ (mPa·s) | Mn |
|---|---|---|---|
| Krasol LBH 2000 | 1100 | 11050 | 1989 |
| Krasol LBH 3000 | 1600 | 16430 | 2931 |
| Poly bd R45HTLO | 1205 | 7000 | 2800 |
| 4-Methylhexahydrophthalic anhydride (HHMPA) from Aldrich | 168.19 | NA | 168.19 |

Formulations of Polybutadiene and HJPMA

Five formulations of carboxyl-terminated polybutadienes were prepared as set forth in Table 3.

TABLE 3

Formulations for preparing carboxyl-terminated polybutadienes

| | Lot no. | | | | |
|---|---|---|---|---|---|
| | 507-162 | 517-120 | 517-121 | 517-123 | 517-129 |
| Krasol LBH 2000 | — | 100 | — | 100 | — |
| Krasol LBH 3000 | — | — | 100 | — | 100 |
| Polybd R45HTLO | 100 | — | — | — | — |
| HHMPA | 13.96 | 15.29 | 10.51 | 15.29 | 10.51 |

Reaction of Carboxyl-Terminated Polybutadienes with Polycarbodiimides in the Presence of Active Reagents The carboxyl-terminated polybutadiene NTX6163 set forth in Table 1 was crosslinked in the presence of a plasticizer, dibutylphthalate (DBP) as shown in Table 5. It was discovered that the addition of OH-containing additives (active ingredients to be released from the controlled release formulation) appeared to have no effect on the curing (Table 4, formulations 2-4). Similarly, the carboxyl-terminated polybutadiene based on Poly bd R45HTLO resin was crosslinked in the presence of fragrance or plasticizer (Table 6). The solvent in commercial Ucarlink was removed and had no significant effect on gelling time (Table 6), but the extra step eliminated the solvent odor for certain applications.

TABLE 4

Chemicals description

| | Description | Eq. wt. | Producer |
|---|---|---|---|
| Ucarlink ™ Crosslinker XL-29SE | A multifunctional carbodiimide | 400-410 (for solid base) | Dow Chemical Company |
| NTX 6163 | HHMPA capped Krasol LBH-3000 | 1777 (acid content = 0.5626 meq/g) | Sartomer |
| Arcol ® Polyol PPG 425 | | | Bayer |
| Pripol 2033 Dimerdiol | | | ICI |
| 2-Ethyl-1,3-hexanediol (EHD) | | | Aldrich |
| Dibutyl phthalate (DBP) | | | Aldrich |

TABLE 5

Gel formulation derived from NTX 6163 in the presence of active agents

| No | Wt. of NTX6163/DBP solution (1/1 by wt.) | XL-29SE/DBP solution (1/1 by wt.) | Additive | Gel time (minutes) at room temperature |
|---|---|---|---|---|
| 1 | 7.6 g | 3.5 g (XL-29SE/DBP) | — | 16.8 |
| 2 | 7.6 g | 3.5 g (XL-29SE/DBP) | 0.76 g PPG425 | 23.1 |
| 3 | 7.6 g | 3.5 g (XL-29SE/DBP) | 0.76 g Pripol 2033 Dimerdiol | 19.7 |
| 4 | 7.6 g | 3.5 g (XL-29SE/DBP) | 0.38 g EHD | 18.0 |

TABLE 6

Gel formulations based on HHMPA-terminated Poly bd R45HTLO resins and polycarbodiimide in the presence of fragrances

| | Sample no. | | | |
|---|---|---|---|---|
| | 11-1 | 11-2 | 13-1 | 13-2 |
| HHMPA-terminated Polybd R45HTLO | 100 | 100 | 100 | 100 |
| Ucarlink XL-29SE (50% solution) | 60.4 | — | 60.4 | 60.4 |
| Ucarlink XL-29SE without solvent | — | 30.2 | — | — |
| Fragrances (lemon grass mint) | 481 | 390.6 | — | — |
| Dibutyl phthalate | — | — | 481 | 481 |
| Wt. % of fragrances in formula | 75 | 75 | 75 | 75 |
| Wt. % of polymer in formula | 20.3 | 25 | 25 | 25 |
| Gel time (minutes) | Overnight | Overnight | 25.1 | 25.5 |
| Curing @ ° C. | 24 | 24.6 | 24.7 | 24.4 |
| Appearance of cured gel | Clear, softer | | Slight yellow, clear | |

As shown in Table 7, the gelling time was shortened when the gelling was carried out at a slightly elevated temperature instead of room temperature, thus increasing the productivity in commercial operation.

TABLE 7

Gel formulations based on HHMPA-terminated Poly bd R45HTLO resins and polycarbodiimide in the presence of fragrances under different gelling temperature

| | Sample no. | |
|---|---|---|
| | 1 | 2 |
| HHMPA-terminated Polybd R45HTLO | 100 | 100 |
| Ucarlink XL-29SE without solvent | 36.26 | 36.26 |
| Fragrances (lemon grass mint) | 408.8 | 408.8 |
| Wt. % of fragrances in formula | 75 | 75 |
| Wt. % of polymer in formula | 25 | 25 |
| Gel time (minutes) | 12.9 | 36.6 |
| Curing @ ° C. | 38.9 | 25 |
| Appearance of cured gel | Yellow, clear gel | |

As shown in Table 8 the gel system was very robust and could be used with other active ingredients such as "Lavender" fragrance.

TABLE 8

Gel formulations based on HHMPA-terminated Poly bd R45HTLO resins and polycarbodiimide in the presence of "Lavender" fragrance.

| | Sample no. | | |
|---|---|---|---|
| | 1 | 2 | 3 |
| Acid-terminated Polybd R45HTLO Resin (PRO 6340) | 100 | 100 | 100 |
| Ucarlink XL-29SE without solvent | 36.26 | 33.24 | 39.24 |
| Fragrances (Lavender) | 408.8 | 399.73 | 417.8 |
| Wt. % of fragrances in formula | 75 | 75 | 75 |
| Wt. % of polymer in formula | 25 | 25 | 25 |
| Gel time (minutes) | 25.0 | 33.7 | 21.5 |
| Curing @ ° C. | 24.0 | 24.5 | 25.0 |
| Appearance of cured gel | Yellow, clear gel | | |

As shown in Table 9, with slightly variation in stoichiometry between acid-terminated polybutadien resin and polycarbodiimide, the hardness of the gel could be altered as desired. The higher equivalent ratios of carbodiimide to acid resulted in harder gels.

TABLE 9

Gel formulations based on HHMPA-terminated Poly bd R45HTLO Resins and polycarbodiimide in the presence of various fragrances

| | Sample no. | | | |
|---|---|---|---|---|
| | 1 | 2 | 3 | 4 |
| Acid-terminated Polybd R45HTLO Resin (PRO 6340) | 100 | 100 | 100 | 100 |
| Ucarlink XL-29SE without solvent | 33.24 | 39.26 | 36.23 | 33.23 |
| Fragrances (Lavender) | 399.8 | 417.8 | — | — |
| Fragrances (Lemon Grass Mint) | — | — | 408.5 | 399.7 |
| Wt. % of fragrances in formula | 75 | 75 | 75 | 75 |
| Wt. % of polymer in formula | 25 | 25 | 25 | 25 |
| Equivalent ratio of carbodiimide/COOH | 1.1 | 1.3 | 1.2 | 1.1 |
| Curing temperature in ° C. | 25 | 25 | 25 | 25 |
| Gel time, minutes (at ° C.) | 33.7 (24.5° C.) | 21.5 (25° C.) | 36.6 (25-26° C.) | 44.9 (39° C.) |
| Relative hardness of gel | Softer | Harder | Harder | Softer |
| Appearance of cured gel | Yellow, clear gel | | | |

Preparation and Curing of Carboxyl-Terminated Poly(Ethylene Glycol)

TABLE 10

Chemicals specifications

| | Lot no. | Mn | Eq. wt |
|---|---|---|---|
| Poly(ethylene glycol) from Aldrich | 11719LO | 1000 | 500 |
| Poly(ethylene glycol) from Aldrich | 15228EB | 579.6 | 289.8 |
| Poly(ethylene glycol) from Aldrich | 05629KB | 2044 | 1022 |
| Hexahydro-4-methylphthalic anhydride (HHMPA) from Aldrich | 15903EA | 168.19 | 168.19 |
| Succinic anhydride from Aldrich | 12121 PA | 100.07 | 100.07 |
| Polyol TP 200 (a triol from Perstorp company) | 3168228 | — | 326.2 |
| Polyol PP 150 (with 4 OH groups from Perstorp company) | 3368004 | — | 195.5 |
| Glutaric anhydride from Aldrich | 04618JB | — | 114.1 |
| 1,2-cyclohexanedicarboxylic anhydride from Aldrich | 09111BU | — | 154.2 |
| Polyethylene glycol 4,000 (Fluka company) | 448936/1 | 3558 | 1779 |

TABLE 11

Preparation of carboxyl-terminated polymers (1.0 equivalents ratio of polyol/anhydride)

| | Chemical and lot no. 550- | | | | | | | |
|---|---|---|---|---|---|---|---|---|
| | 12 | 13 | 14 | 19 | 23 | 24 | 26 | 31 | 32 |
| Poly(ethylene glycol) (11719LO) | 100 | | | | | | | | |
| Poly(ethylene glycol) (15228EB) | | 100 | | 100 | | | | | |
| Poly(ethylene glycol) (05629KB) | | | 100 | | | | | | |
| Polyol TP 200 (3168228) | | | | | 100 | | 100 | | |
| Polyol PP 150 (3368004) | | | | | | | | 100 | 100 |
| Polyethylene glycol 4000 (448936/1) | | | | | | 100 | | | |
| HHMPA (15903EA) | 33.64 | 58.04 | 16.46 | | 51.56 | 9.454 | | | |
| Succinic anhydride (12121PA) | | | | 34.53 | | | 27.63 | | |
| Glutaric anhydride (04618JB) | | | | | | | | 58.36 | |
| 1,2-cyclohexanedicarboxylic anhydride (09111BU) | | | | | | | | | 78.87 |

Preparative Procedures and Product Analysis
1. PEG or Polyol was dried and degassed in vacuum at <1333 Pa at 95° C. for 2 hrs.
2. Anhydride was charged into resin kettle
3. Reaction was held at 100-105° C. with stirring and $N_2$ slow purge for 3 hrs.
4. Determination of acid content of products

TABLE 12

Characterization of carboxyl-terminated polyethylene glycols

|  | Lot no. | Eq. Wt. | Carboxyl content (meq./g) |
|---|---|---|---|
| Carboxyl terminated PEG | 550-13 | 458 | 2.184 |
| Carboxyl terminated PEG | 550-12 | 668 | 1.497 |
| Carboxyl terminated PEG | 550-14 | 1197 | 0.835 |
| Carboxyl terminated PEG | 550-19 | 390.8 | 2.559 |
| Carboxyl terminated PEG | 550-23 | 492.1 | 2.032 |
| Carboxyl terminated PEG | 550-24 | 1926.8 | 0.519 |
| Carboxyl terminated Polyol TP200 | 550-26 | 463 | 2.159 |
| Carboxyl terminated Polyol PP 150 | 550-31 | 304 | 3.294 |
| Carboxyl terminated Polyol PP 150 | 550-32 | 339 | 2.953 |
| De-ionized water |  |  |  |
| XL-29SE (50% solution in DOWANOL PMA) | QI1355T812 | Eq. Wt. = 810 (for solution) | |

Miscibility and Physical Property of Carboxyl-Terminated Poly(Ethylene Glycol) in Water The water miscibility of the acid-capped polyethylene glycol depends on the structure of the capping agent used and the molecular weight of PEG. When the PEG molecular weight is reduced, the capping agent used needs to be more polar to render the resulting carboxyl-terminated PEG (CTPEG) water soluble (Table 13).

TABLE 13

Miscibility of carboxyl-terminated PEG with water

| Lot no. of CTPEG | Anhydride used | Mn of PEG | Carboxyl content of CTPEG (meq/g) | Eq. wt. of CTPEG | Appearance of CTPEG at room temperature | Miscibility of CTPEG in water |
|---|---|---|---|---|---|---|
| 550-19 | Succinic | 580 | 2.559 | 390.8 | Clear liquid | Miscible |
| 550-13 | Hexahydro-4-methylphthalic | 580 | 2.184 | 458 | Clear liquid | Not miscible |
| 550-12 | Hexahydro-4-methylphthalic | 1000 | 1.497 | 668 | Cloudy liquid | Miscible |
| 550-14 | Hexahydro-4-methylphthalic | 2044 | 0.835 | 1197 | Cloudy solid | Miscible |
| 550-23 | Hexahydro-4-methylphthalic | NA | 2.032 | 492.1 | Clear liquid | Not miscible |
| 550-24 | Hexahydro-4-methylphthalic | 3558 | 0.519 | 1926.8 | Cloudy solid | Miscible |
| 550-26 | Succinic | — | 2.159 | 463 | Clear liquid | Miscible |
| 550-31 | Glutaric | — | 3.294 | 304 | Clear liquid | Miscible |
| 550-32 | 1,2-cyclohexanedicarboxylic | — | 2.953 | 339 | High viscous liquid | Not miscible |

Gel Formation of Carboxyl-Terminated Polymers with Ucarlink™ XL-29SE in the Presence of Water The water-containing gels were formed by reaction between carboxyl-capped PEGs and polycarbodiimide (Table 14).

TABLE 14

Aqueous gel formation from carboxyl-terminated PEG and polycarbodiimide

| Checking no. | Lot no. of CTPEG | Eqs ratio of XL-29SE/CTPEG | Wt. % of H2O | Wt. % of polymers | Situation of gelling |
|---|---|---|---|---|---|
| 550-20-5 | 550-19 | 3.0 | 29.86 | 39.93 | Softer gel |
| 550-20-7 | 550-19 | 4.0 | 24.86 | 41.62 | Gelled |
| 550-20-11 | 550-19 | 5.0 | 21.29 | 42.82 | Firmer gel |
| 550-16-7 | 550-12 | 2.0 | 39.25 | 39.25 | Soft gel |
| 550-16-10 | 550-12 | 4.0 | 53.12 | 27.44 | Soft gel |
| 550-16-5 | 550-14 | 1.0 | 50.00 | 39.90 | Soft gel |
| 550-16-11 | 550-14 | 3.0 | 62.40 | 25.00 | Firmer gel |
| 550-25-3 | 550-24 | 1.5 | 46.55 | 43.11 | Gelled |
| 550-25-2 | 550-24 | 2.0 | 43.55 | 43.55 | Soft gel |
| 550-25-6 | 550-24 | 4.0 | 61.38 | 26.51 | Soft gel |
| 550-28-2 | 550-26 | 2.0 | 37.93 | 37.93 | Gelled |
| 550-28-6 | 550-26 | 5.0 | 45.85 | 29.87 | Soft gel |
| 550-36-1 | 550-31 | 2.0 | 36.67 | 36.67 | Gelled |
| 550-36-3 | 550-32 | 4.0 | 48.53 | 27.94 | Gelled |
| 550-36-3 | 550-32 | 5.0 | 43.43 | 30.26 | Gelled |

While preferred embodiments of the invention have been described and illustrated here, various changes, substitutions and modifications to the described embodiments will become apparent to those of ordinary skill in the art without thereby departing from the scope and spirit of the invention.

What is claimed is:

1. A continuous release composition comprising an elastomeric matrix and at least one active agent, the active agent being released from the matrix into the environment substantially continuously over an extended period of time and the said matrix being the reaction product of a carboxyl-terminated polymer with a polycarbodiimide.

2. The composition of claim 1 wherein the molar ratio of polycarbodiimide to carboxyl-terminated polymer is 0.7:1 to 6:1.

3. The composition of claim 1 wherein the carboxyl-terminated polymer is hydrophobic.

4. The composition of claim 1 wherein the carboxyl-terminated polymer is hydrophobic and a major component is selected from the group consisting of carboxyl-terminated polybutadiene, carboxyl-terminated polyisoprene, carboxyl-terminated copolymers of butadiene with acrylonitrile, carboxyl-terminated copolymers of butadiene with styrene, carboxyl-terminated copolymers of isoprene with acrylonitrile, carboxyl-terminated copolymers of isoprene with styrene, and mixtures thereof.

5. The composition of claim 4 wherein the major component is at least 90% of the polymer, by weight.

6. The composition of claim 1 wherein the carboxyl-terminated polymer is hydrophobic and the molar ratio of polycarbodiimide to carboxyl-terminated polymer is 0.7:1 to 1.4:1.

7. The composition of claim 1 wherein the carboxyl-terminated polymer is hydrophobic and has an average molecular weight in the range of 1000 to 20,000.

8. The composition of claim 1 wherein the carboxyl-terminated polymer is hydrophilic and a major component is selected from the group consisting of carboxyl-terminated polyethylene oxides and carboxyl-terminated polyether polyols.

9. The composition of claim 8 wherein the major component is at least 90% of the polymer, by weight.

10. The composition of claim 1 wherein the carboxyl-terminated polymer is the reaction product of a mixture of alkylene oxides comprising ethylene oxide and an alkylene oxide having 3-6 carbons atoms.

11. The composition of claim 1 wherein the carboxyl-terminated polymer is the reaction product copolymer of a mixture of alkylene oxides comprising ethylene oxide and at least one alkylene oxide having 3-6 carbons atoms and wherein the alkylene oxide having 3-6 carbons atoms comprises more than 50 mole percent of said copolymer.

12. The composition of claim 1 wherein the carboxyl-terminated polymer is the reaction product copolymer of a mixture of alkylene oxides comprising ethylene oxide and at least one alkylene oxide having 3-6 carbons atoms and wherein the alkylene oxide having 3-6 carbons atoms comprises more than 50 mole percent of said copolymer and the copolymer has a molecular weight from 400 to 20,000.

13. The composition of claim 1 wherein the polycarbodiimide is selected from the group consisting of aromatic, cycloaliphatic, aliphatic and heterocyclic carbodiimides, and mixtures of thereof.

14. The composition of claim 1 wherein polycarbodiimide has an average functionality of at least 2.

15. The composition of claim 1 further comprising one or more inert components which do not interfere in the carboxylic acid-carbodiimide reaction.

16. The composition of claim 1 further comprising one or more inert components which do not interfere in the carboxylic acid-carbodiimide reaction selected from the group consisting of fillers, plasticizers, stabilizers, pigments, and fungicides.

17. The composition of claim 1 wherein the carboxyl-terminated polymer has a molecular weight of 1000 to 10,000 and is a carboxyl-terminated polybutadiene or a carboxyl-terminated polyisoprene and an average carboxylic acid functionality in the range of 1.8 to 8.0.

18. The composition of claim 1 wherein the at least one active agent is dissolved in the matrix.

19. The composition of claim 1 wherein the at least one active agent is dispersed in the matrix.

20. The composition of claim 1 wherein the at least one active agent is present in an amount of about 10% to 90% by weight based on the total weight of the elastomeric matrix.

21. The composition of claim 1 wherein the at least one active agent comprises a fragrance.

22. The composition of claim 1 in the form of a gel.

23. An article formed from the composition of claim 1.

24. Article according to claim 23 comprising an elastomeric matrix and at least one biologically or nonbiologically active agent contained in the matrix, the said active agent being released from the matrix into the environment substantially continuously over an extended period of time and the said matrix being formed by a process comprising reacting a carboxyl-terminated polymer, selected from either hydrophobic or hydrophilic carboxyl terminated polymers, with a polycarbodiimide.

25. Article according to claim 24 wherein a)the said hydrophobic carboxyl-terminated polymer comprises a major component selected from the group consisting of carboxyl-terminated polybutadiene, carboxyl-terminated polyisoprene, carboxyl-terminated copolymers of butadiene with acrylonitrile, carboxyl-terminated copolymers of butadiene with styrene, carboxyl-terminated copolymers of isoprene with acrylonitrile, carboxyl-terminated copolymers of isoprene with styrene, and mixtures of the above, the carboxylic acid terminated polymer having an average molecular weight in the range of 1000 to 20000; and b) the said hydrophilic carboxyl-terminated polymer comprises a major component selected from the group consisting of carboxyl-terminated polyethylene oxides, carboxyl-terminated polyether polyols which are copolymers of ethylene oxide and of an alkylene oxide having 3-6 carbons atoms, in an amount of not more than 50 mole percent of said copolymer and having molecular weight from 400 to 20000.

26. The article of claim 23 in a form which is suitable for either biological or non-biological action.

27. The article of claim 23 in a form suitable for providing insecticidal, fungicidal, deodorant, molluscidal, anticorrosive, antistatic, pheromone, or antiseptic action over an extended period of time.

28. Article according to claim 23, wherein the said active agent is selected from pheromones.

29. A method of providing insecticidal, fungicidal, deodorizing, mollusicidal, anticorrosive, antistatic, pheromonal, or antiseptic action over an extended period of time comprising providing an article of claim 23 wherein the active agent is an insecticide, fungicide, deodorant, mullusicicide, anticorrosive, antistatic, pheromone, antiseptic, or a mixture of such agents.

30. A method of preparing a composition of claim 1 comprising reacting the carboxyl-terminated polymer with the polycarbodiimide in the presence of the active agent.

31. The composition of claim 1 wherein the carboxyl-terminated polymer is a carboxyl-terminated polyethylene oxide.

* * * * *